(12) United States Patent
Wada

(10) Patent No.: US 11,751,969 B2
(45) Date of Patent: Sep. 12, 2023

(54) STORAGE CONTAINER, PACKAGING MEMBER, AND MEDICAL INSTRUMENT SET

(71) Applicant: TERUMO KABUSHIKI KAISHA, Tokyo (JP)

(72) Inventor: Satoshi Wada, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 610 days.

(21) Appl. No.: 16/825,386

(22) Filed: Mar. 20, 2020

(65) Prior Publication Data
US 2020/0214782 A1  Jul. 9, 2020

Related U.S. Application Data

(63) Continuation of application No. PCT/JP2018/039021, filed on Oct. 19, 2018.

(30) Foreign Application Priority Data

Oct. 20, 2017 (JP) ................................ 2017-203972

(51) Int. Cl.
| | |
|---|---|
| *A61B 50/30* | (2016.01) |
| *A61M 25/06* | (2006.01) |
| *A61M 25/00* | (2006.01) |
| *A61M 25/09* | (2006.01) |
| *A61M 39/08* | (2006.01) |
| *A61M 39/06* | (2006.01) |
| *B65D 81/20* | (2006.01) |

(52) U.S. Cl.
CPC ......... *A61B 50/30* (2016.02); *A61M 25/0606* (2013.01); *A61M 25/0097* (2013.01);
(Continued)

(58) Field of Classification Search
CPC ........... A61B 50/30; A61B 2050/3008; A61M 25/0606; A61M 25/0097; A61M 25/0618;
(Continued)

(56) References Cited

U.S. PATENT DOCUMENTS

| | | | | |
|---|---|---|---|---|
| 6,896,141 | B2 * | 5/2005 | McMichael | A61B 50/33 206/370 |
| 2004/0031721 | A1 * | 2/2004 | Mann | A61B 10/04 206/570 |
| 2006/0011501 | A1 * | 1/2006 | Itou | A61M 25/002 206/370 |

FOREIGN PATENT DOCUMENTS

| | | |
|---|---|---|
| CN | 103945818 A | 7/2014 |
| EP | 2 774 596 A1 | 9/2014 |

(Continued)

OTHER PUBLICATIONS

Office Action (The First Office Action) dated Jul. 29, 2021, by the State Intellectual Property Office of People's Republic of China in corresponding Chinese Patent Application No. 201880055123.1 and an English Translation of the Office Action. (13 pages).

(Continued)

*Primary Examiner* — Lauren P Farrar
*Assistant Examiner* — Hamza A Darb
(74) *Attorney, Agent, or Firm* — BUCHANAN INGERSOLL & ROONEY PC

(57) ABSTRACT

A storage container, a packaging member, and a medical instrument set are reduced in size and can reduce the burden of preparing medical instruments. The storage container includes side face parts surrounding a first space and a second space for accommodating an introducer, a first storage part in which a catheter hub is disposed, a second storage part in which a tubular member is disposed in a state in which a connector unit is disposed in the second space, and a third storage part in which a dilator hub is disposed. The third storage part is disposed between the first storage part and the second storage part.

21 Claims, 6 Drawing Sheets

(52) U.S. Cl.
    CPC ..... *A61M 25/0618* (2013.01); *A61M 25/0662* (2013.01); *A61M 25/09* (2013.01); *A61M 39/08* (2013.01); *A61M 2025/0681* (2013.01); *A61M 2039/062* (2013.01)

(58) Field of Classification Search
    CPC .. A61M 25/0662; A61M 25/09; A61M 39/08; A61M 2025/0681; A61M 2039/062; A61M 25/002; A61M 25/06; B65D 81/20
    See application file for complete search history.

(56) References Cited

FOREIGN PATENT DOCUMENTS

| | | |
|---|---|---|
| JP | H1099441 A | 4/1998 |
| JP | 2017528286 A | 9/2017 |
| WO | 2013018770 A1 | 2/2013 |
| WO | 2014076819 A1 | 5/2014 |

OTHER PUBLICATIONS

An English Translation of the International Search Report (Form PCT/ISA/210) and the Written Opinion of the International Searching Authority (Form PCT/ISA/237) dated Nov. 27, 2018, by the Japan Patent Office in corresponding International Application No. PCT/JP2018/039021. (10 pages).

International Search Report (PCT/ISA/210) dated Nov. 27, 2018, by the Japanese Patent Office as the International Searching Authority for International Application No. PCT/JP2018/039021.

* cited by examiner

STORAGE CONTAINER, PACKAGING MEMBER, AND MEDICAL INSTRUMENT SET

CROSS-REFERENCES TO RELATED APPLICATIONS

This application is a continuation of International Application No. PCT/JP2018/039021 filed on Oct. 19, 2018, which claims priority to Japanese Patent Application No. 2017-203972 filed on Oct. 20, 2017, the entire content of both of which is incorporated herein by reference.

FIELD OF THE INVENTION

The present invention generally relates to a storage container, a packaging member, and a medical instrument set.

BACKGROUND DISCUSSION

Medical instruments such as catheters and introducers used for operations and diagnosis are transported to medical sites while being accommodated in dedicated storage containers and packaging members. Health care workers such as doctors and nurses take out medical instruments from storage containers and packaging members and use them for operations and diagnoses.

For storage and transport of medical instruments, for example, a box-shaped storage container as described in Japanese Patent Application Publication No. H10-099441 is used. This storage container accommodates a medical instrument enclosed in a bag together with the bag.

SUMMARY

The above-described storage container is configured to accommodate a medical instrument in a space formed inside the box. Therefore, although the above-mentioned storage container has a simple structure, there is room for improvement in a variety of ways such as the following points.

For example, when accommodating a plurality of medical instruments in one storage container, an elongated tube member (such as a tube in fluid communication with a lumen of a catheter) provided in the medical instrument is disposed in a storage container so as not to interfere with other medical instruments in order to prevent kink or the like from occurring in the tube member. However, in the case where the tube member is accommodated in the storage container in consideration of the disposition relationship with other medical instruments, the storage container needs to have a correspondingly large space. Thereby, the storage container becomes large in volume and large in size.

Further, for example, when a medical instrument (such as an introducer) into which a plurality of constituent members will be assembled before use is accommodated in the above-described storage container, an operator such as a doctor (hereinafter, referred to as an operator) takes out the constituent members of the medical instrument from the storage container and assembles the constituent members to form the instrument. At that time, the operator performs an operation of adjusting the orientation of the constituent members in consideration of the direction and posture of assembling the constituent members of the medical instrument. Therefore, when the storage container is used for accommodating a medical instrument including a plurality of constituent members, the preparation of the medical instrument becomes complicated.

The storage container, packaging member, and medical instrument set disclosed here is reduced in size and can reduce the burden of preparing medical instruments.

A storage container according to one aspect is configured to accommodate a medical instrument that includes a catheter member and a dilator member, wherein the catheter member includes a catheter main body, a catheter hub disposed at a proximal portion of the catheter main body, a tubular member disposed on a side face of the catheter hub and communicating with a lumen of the catheter hub and a connector unit disposed at an end portion of the tubular member opposite to the catheter hub, and wherein the dilator member includes a dilator main body insertable into a lumen of the catheter main body and a dilator hub disposed at a proximal portion of the dilator main body. The storage container comprises: a side face part surrounding a space that is configured to accommodate the medical instrument; a first storage part configured to receive the catheter main body or the catheter hub; a second storage part configured to receive the tubular member while the connector unit is disposed in the space; and a third storage part configured to receive the dilator main body or the dilator hub; wherein the third storage part is disposed between the first storage part and the second storage part.

In the above-described storage container, the catheter main body or the catheter hub is disposed in the first storage part, the tube member is disposed in the second storage part and the dilator main body or the dilator hub is disposed in the third storage part. Further, the third storage part is located between the first storage part and the second storage part. Therefore, the above-described storage container can three-dimensionally accommodate the catheter member and the dilator member, and can reduce the volume (size) of the storage container. Further, since the distance between the catheter main body or the catheter hub disposed in the first storage part and the tube member disposed in the second storage part increases, a kink of the tube member due to a decrease in the distance between the catheter main body or the catheter hub and the tube member can be prevented. Furthermore, in the above-described storage container, the catheter member and the dilator member can be disposed close to each other in a state in which the orientation of the catheter member and the orientation of the dilator member forming an assembly with the catheter member are in the same direction, so that the operator can easily form an assembly including the catheter member and the dilator member.

According to another aspect, a packaging member includes a medical instrument that comprises a catheter member and a dilator member, wherein the catheter member includes a catheter main body, a catheter hub disposed at a proximal portion of the catheter main body, a tubular member disposed on a side face of the catheter hub and communicating with a lumen of the catheter hub and a connector unit disposed at an end portion of the tubular member opposite to the catheter hub, and wherein the dilator member includes a dilator main body insertable into a lumen of the catheter main body and a dilator hub disposed at a proximal portion of the dilator main body. The packaging member comprises: a storage container comprising: a side face part surrounding a space in which is disposed the connector unit; a first storage part at which is stored the catheter main body or the catheter hub, a part of the catheter main body extending into the space; a second storage part at which is received the tubular member; a third storage part at which is stored the dilator main body or the dilator hub; and the third storage part being disposed between the first storage part and the second storage part. The space and the medical instrument are enclosed and prevented from communicating with outside the packaging member so that the space and the medical instrument remain in a sterilized state when sterilized.

In accordance with another aspect, a medical instrument set comprises: a medical instrument comprised of a catheter member and a dilator member, wherein the catheter member includes a catheter main body, a catheter hub disposed at a proximal portion of the catheter main body, a tubular member disposed on a side face of the catheter hub and communicating with a lumen of the catheter hub and a connector unit disposed at an end portion of the tubular member opposite to the catheter hub, and wherein the dilator member includes a dilator main body insertable into a lumen of the catheter main body and a dilator hub disposed at a proximal portion of the dilator main body. The medical instrument set also comprises a storage container comprising: a side face part surrounding a space; a first storage part, a second storage part and a third storage part; the third storage part being disposed between the first storage part and the second storage part; with the connector unit being located in the space, the catheter main body or the catheter hub being stored in the first storage part while a part of the catheter main body extends into the space, and the tubular member being stored in the second storage space. In addition, an accessory is accommodated in the space and has a width smaller than a maximum width of the connector unit in a direction intersecting an axial direction of the tube member.

DETAILED DESCRIPTION

Set forth below with reference to the accompanying drawings is a detailed description of embodiments and modification examples of a storage container, a packaging member, and a medical instrument set representing examples of the inventive storage container, packaging member, and medical instrument set disclosed here. The dimensions or scales on the drawings may be exaggerated or different from actuality/reality for convenience of description and illustration.

FIGS. 1 to 4 are views showing a medical instrument set 10 according to the present embodiment. An illustration of the accessories 330, 340, and 350 is omitted in FIG. 3.

Figure 1:
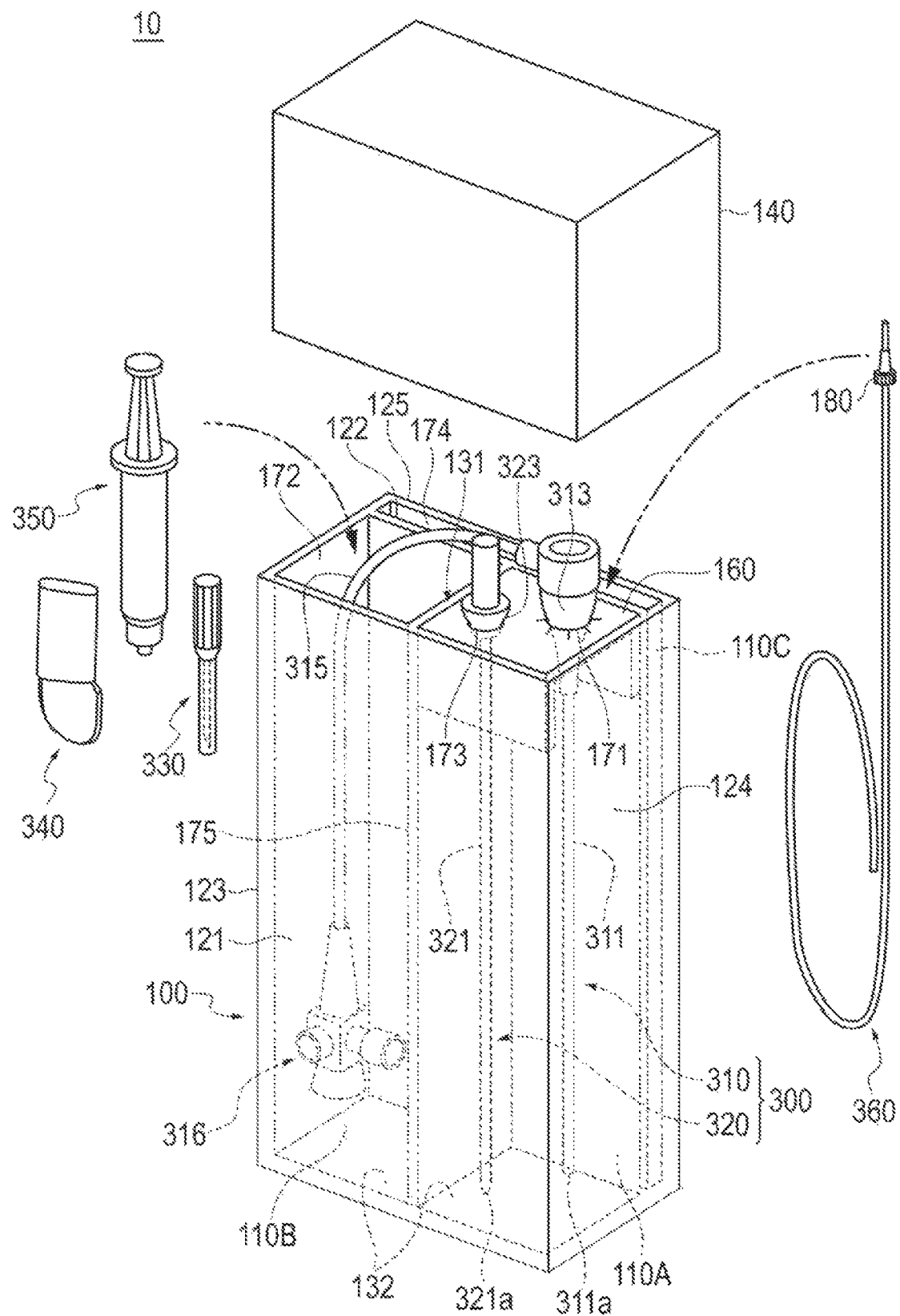
FIG. 1 is a schematic perspective view showing a medical instrument set according to an embodiment of the present invention.
Figure 2:
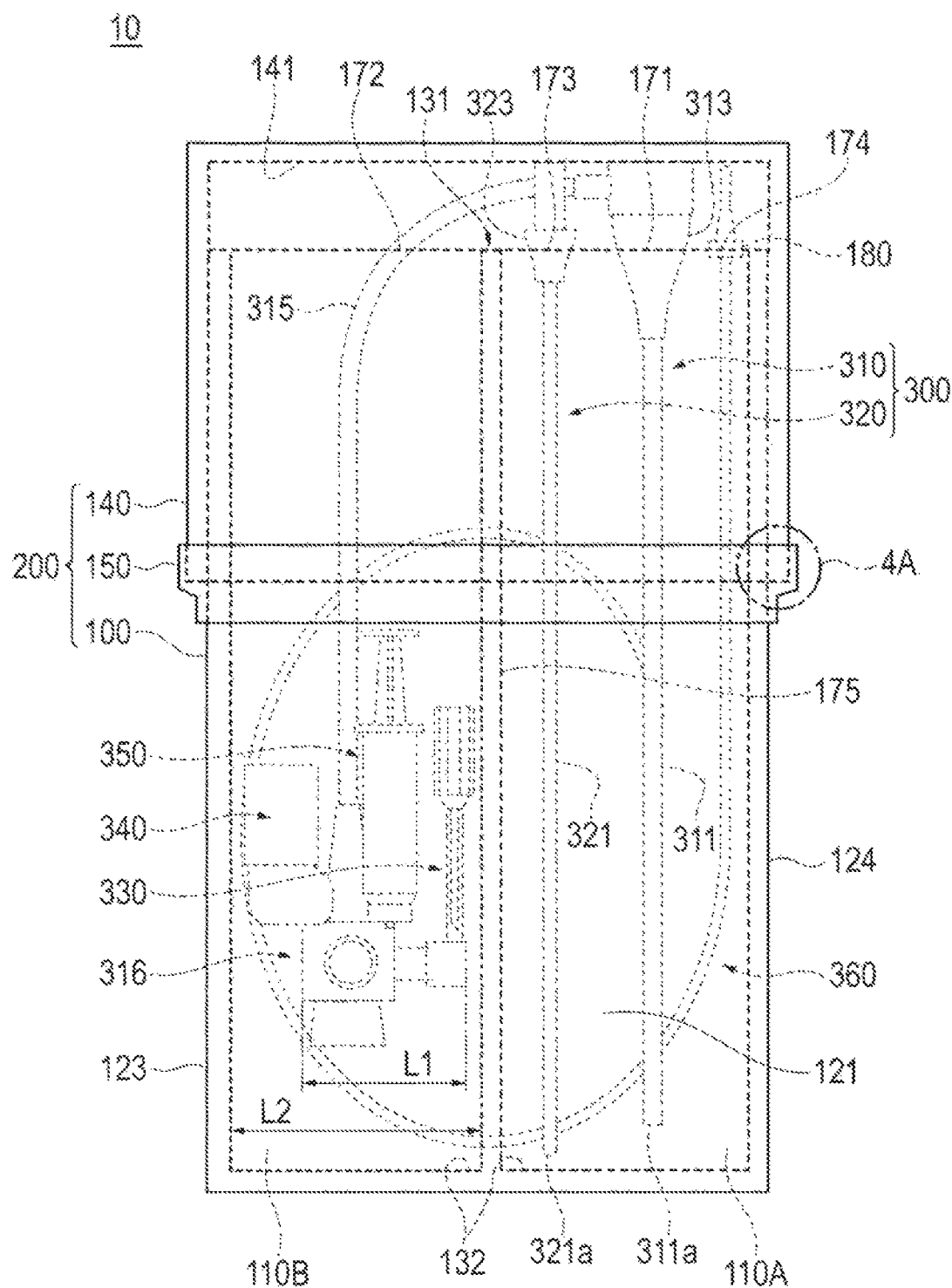
FIG. 2 is a front view of the medical instrument set according to the embodiment.

As shown in FIGS. 1 and 2, the medical instrument set 10 includes an introducer (corresponding to "medical instrument") 300 including a catheter member 310 and a dilator member 320, accessories 330, 340, and 350 used for a procedure using the introducer 300, a guide wire 360, and a storage container 100 for accommodating the introducer 300, the guide wire 360 and the accessories 330, 340, and 350.

In the present embodiment, the storage container 100 forms, as shown in FIG. 2, a packaging member 200 for accommodating and storing the storage objects 300, 330, 340, 350, and 360, which includes the storage container 100, a cap member 140 used with the storage container 100, and a seal member 150 (not shown in FIG. 1) interlocking the storage container 100 with the cap member 140.

The medical instrument set 10 will be described.

(Introducer)

As shown in FIGS. 1 and 2, the introducer 300 has the catheter member 310 and the dilator member 320. During the procedure, the operator punctures a biological lumen such as a blood vessel in a state in which the dilator member 320 is assembled to the catheter member 310. Thereafter, the operator removes the dilator member 320 from the catheter member 310, and indwells the catheter member 310 in the biological lumen. The catheter member 310 can be used as an introduction path for introducing a medical instrument or the like for diagnosing/treating a lesion area while being indwelled in a biological lumen.

Before use, the introducer 300 is accommodated in the storage container 100 in a state in which the catheter member 310 and the dilator member 320 are separated as shown in FIGS. 1 and 2.

In the description of the present specification, in the catheter member 310 and the dilator member 320, the side to be inserted into a biological lumen such as a blood vessel is referred to as the "distal side" or the "distal end", and the opposite side is referred to as the "proximal side" or the "proximal end". Further, the distal end (most distal end) of the catheter member 310 and the dilator member 320 and the vicinity of the distal end are referred to as "distal portion", and the proximal end (most proximal end) and the vicinity thereof are referred to as "proximal portion".

The catheter member 310 will be described.

As shown in FIGS. 1 and 2, the catheter member 310 is used, for example, to insert a medical instrument such as a treatment catheter or the guide wire 360 into the inside (lumen) and introduce them into a biological lumen.

The catheter member 310 has an elongated catheter main body (tubular part) 311, a catheter hub 313 disposed at a proximal portion of the catheter main body 311, a tubular member or tube 315 disposed on or projecting from the side face side (side face) of the catheter hub 313 and communicating with the lumen of the catheter hub 313, and a connector unit 316 disposed at the end portion of the tubular member 315 opposite to the catheter hub 313.

The catheter main body 311 is formed of a substantially cylindrical tubular member having flexibility. Examples of a material constituting the catheter main body 311 include a polymer material such as polyolefin (for example, polyethylene, polypropylene, polybutene, an ethylene-propylene copolymer, an ethylene-vinyl acetate copolymer, an ionomer, and a mixture of at least two thereof), a polyolefin elastomer, a cross-linked body of polyolefin, polyvinyl chloride, polyamide, a polyamide elastomer, polyester, a polyester elastomer, polyurethane, a polyurethane elastomer, fluorine resin, polycarbonate, polystyrene, polyacetal, polyimide, and polyetherimide, and a mixture thereof.

One end of the tubular member 315 is liquid-tightly connected to a side port disposed at the catheter hub 313. The tubular member 315 can be made of a material having lower flexural rigidity than the catheter main body 311. Examples of such a material include vinyl chloride.

Inside the catheter hub 313, a valve body for preventing blood or the like from leaking from a proximal portion of the catheter hub 313 in a state in which a dilator main body 321 is inserted through the catheter main body 311 is disposed. Further, at the distal side of the catheter hub 313, a strain relief portion that covers the proximal portion of the catheter main body 311 is disposed.

In the present embodiment, the connector unit 316 is configured as a three-way stopcock. The other end of the tubular member 315 is connected to the connector unit 316 in a liquid-tight manner.

As shown in FIG. 2, a maximum width L1 of the connector unit 316 is larger than the width of the accessory 330, is larger than the width of the accessory 340, and is larger than the width of the accessory 350. The maximum width L1 of the connector unit 316 is a maximum value of a dimension in a direction intersecting the axial direction (the vertical direction in FIG. 2) of the tube member 315 in the front view shown in FIG. 2. The widths of the accessories 330, 340, and 350 are the widths in the direction intersecting the longitudinal direction (the vertical direction in FIG. 2) of the accessories 330, 340, and 350 in the front view shown in FIG. 2.

The dilator member 320 will now be described.

As shown in FIGS. 1 and 2, the dilator member 320 has the dilator main body 321 that can be inserted into the lumen of the catheter main body 311 and a dilator hub 323 disposed at the proximal portion of the dilator main body 321.

The dilator main body 321 is formed of a tubular member having higher flexural rigidity than the catheter main body 311. When the dilator main body 321 is inserted into the catheter main body 311, a distal end 321a of the dilator main body 321 protrudes distally from or beyond an opening portion at a distal end 311a of the catheter main body 311. Therefore, as shown in FIG. 2, the overall length (length in the axial direction) of the dilator main body 321 is longer than the overall length (length in the axial direction) of the catheter main body 311.

(Accessories)

In the present embodiment, the accessory 330 is an introduction needle, the accessory 340 is a scalpel, and the accessory 350 is a syringe. The introduction needle 330 and the scalpel 340 are accommodated in the storage container 100 in a state in which the cap member is attached. The syringe 350 is accommodated in the storage container 100 in a state in which a discharge such as a liquid is not stored (unused state). The type, shape, size, number, and the like of the products to be accommodated in the storage container 100 are not particularly limited as long as the accessories have a width smaller than the maximum width L1 of the connector unit 316.

As shown in FIG. 2, the accessories 330, 340, and 350 are supported on the connector unit 316 of the catheter member 310 in a state of being accommodated in a second space 110B of the storage container 100. Thereby, the connector unit 316 can prevent the accessories 330, 340, and 350 from moving toward a lower face part 132 beyond the connector unit 316.

(Guide Wire)

The guide wire 360 has an elongated shape with flexibility. As the guide wire 360, a guide wire known in the medical field can be used. An inserter 180 is attached to the distal portion of the guide wire 360. The distal portion of the guide wire 360 protrudes from the inserter 180 by a predetermined length. The inserter 180 can be used as a fixing member for fixing the guide wire 360 to the storage container 100, as described later.

The material constituting the inserter 180 is not particularly limited. Examples thereof include polyolefin such as polyethylene and polypropylene, polyvinyl chloride, polyester (PET, PBT, etc.), polyamide, polyimide, polyurethane, polystyrene, silicone resin, and the like can be used.

When the guide wire 360 is accommodated in the storage container 100 in a curved or wound state, for example, the guide wire 360 itself may be put in a bag or a holder tube to prevent the guide wire 360 in a curved or wound state from spreading out (unwinding), or to protect the guide wire 360 from surrounding members. Further, the holder tube may include, for example, a fixture for maintaining the holder tube in a curved or wound state in a state in which the guide wire 360 is curved or wound. The guide wire 360 can be stored in a fourth storage part 174 of the storage container 100 in a state of being accommodated in the bag or the holder tube as described above.

Next, the storage container 100 and the packaging member 200 will be described.

Figure 3:
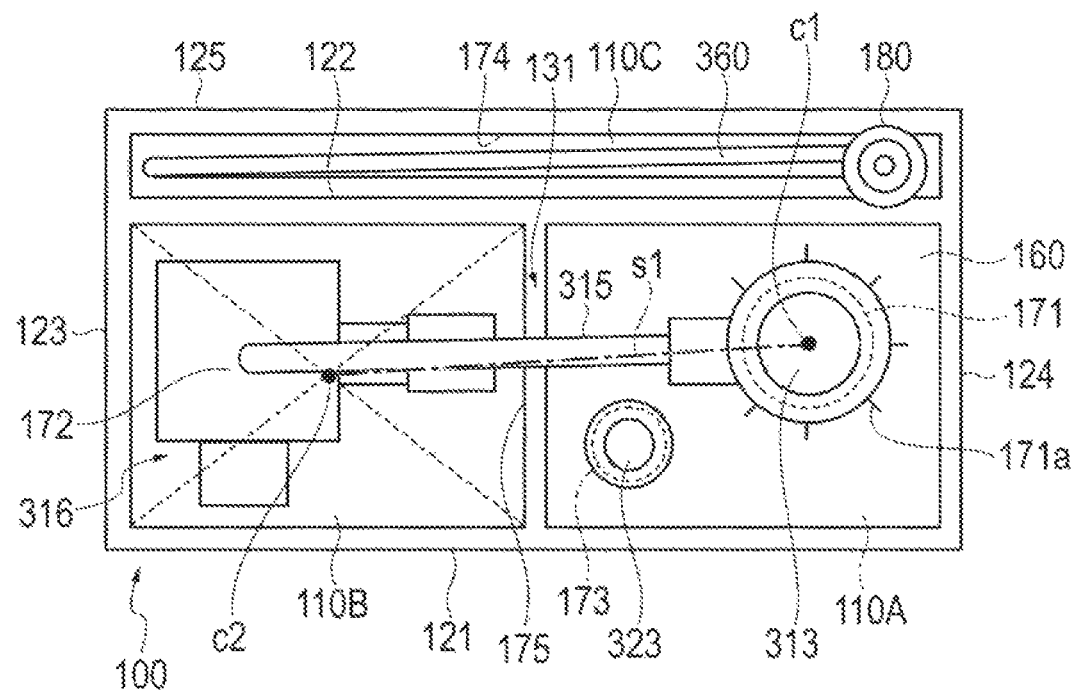
FIG. 3 is a top view of the medical instrument set according to the embodiment with a cap member removed.

As shown in FIGS. 1 to 3, the storage container 100 includes a first space 110A (corresponding to a "space") that accommodates the catheter main body 311 and the dilator main body 321, the second space 110B (corresponding to a "space") that accommodates the tubular member 315 and the accessories 330, 340, and 350, and a side face part surrounding the first space 110A and the second space 110B. In the illustrated embodiment disclosed by way of example, the side face part may include a first side face part (wall) 121, a second side face part (wall) 122, a third side face part (wall) 123, and a fourth side face part (wall) 124 surrounding the first space 110A and the second space 110B.

As shown in FIG. 1, the storage container 100 includes an upper face part (upper face) 131 formed or positioned inside each of the side face parts 121, 122, 123, and 124 (on the first space 110A and the second space 110B side), and one end (upper end side) of each of the side face parts 121, 122, 123, and 124, and a lower face (lower face) part 132 facing toward the upper face part 131 with the side face parts 121, 122, 123, and 124 interposed therebetween. As shown in FIG. 1, the storage container may be a parallelepiped and may be configured so that the largest dimension of the storage container 100 is the vertical or height direction (i.e., the dimension from the upper face 131 to the lower face 132.

The vertical direction in the present specification is defined for convenience in an example of the used state of the storage container 100 shown in FIG. 2. Therefore, the positional relationship in the vertical direction described in the specification does not limit the positional relationship of the storage container 100 in the used state. For example, the storage container 100 can be transported and stored in a state in which the upper face part 131 and the lower face part 132 are disposed in the horizontal direction in FIG. 2 or in a state in which the storage container 100 is inclined.

The upper face part 131 is formed with an opening portion opened to face the outside of the storage container 100. The lower face part 132 is formed with a bottom portion that separates the lower face side of the storage container 100 from the outside.

The first side face part 121 (disposed on the front side in FIG. 1) and the second side face part 122 (disposed on the back side in FIG. 1) are disposed substantially parallel to each other and face each other. The third side face part 123 (disposed on the left side in FIG. 2) and the fourth side face part 124 (disposed on the right side in FIG. 2) are disposed substantially parallel to each other and face each other.

As shown in FIG. 2, the first space 110A and the second space 110B are partitioned by a partition part 175. The partition part 175 is disposed substantially parallel to the side face parts 123 and 124.

As shown in FIG. 1, a support part 160 is disposed near the upper face part 131 of the first space 110A. The support part 160 has a first storage part 171 in which the catheter hub 313 is disposed, and a third storage part 173 in which the dilator hub 323 is disposed.

By way of example, the catheter main body 311 can be disposed in the first storage part 171. Further, for example, the dilator main body 321 can be disposed in the third storage part 173.

As shown in FIG. 1, a second storage part 172 in which the tube member 315 is disposed is formed in a part of the upper face part 131 in a state in which the connector unit 316 is disposed in the second space 110B.

As shown in FIGS. 1 and 3, the first storage part 171 is formed on the upper face part 131 side by a first hole part that allows the first space 110A to communicate with the outside of the first space 110A. Further, the third storage part 173 is formed on the upper face part 131 side by a third hole part that allows the first space 110A to communicate with the outside of the first space 110A.

The first storage part 171 (first hole part or first hole) and the third storage part 173 (third hole part or third hole) are formed by through-holes formed in the support part 160. The first storage part 171 and the third storage part 173 have a substantially circular shape when viewed from above as shown in FIG. 3.

In the first storage part 171, the inner edge of the first storage part 171 is attached to the outer side face of the catheter hub 313 (the strain relief portion provided in the catheter hub 313). The diameter of the first storage part 171 is adjusted so that the catheter hub 313 can be held. Note that, the specific position of the catheter hub 313 or the catheter main body 311 disposed in the first storage part 171 is not particularly limited.

In the third storage part 173, the inner edge of the third storage part 173 attaches to the outer side face of the dilator hub 323. The diameter of the third storage part 173 is adjusted so that the dilator hub 323 can be held. Note that, the specific position of the dilator hub 323 or the dilator main body 321 disposed in the third storage part 173 is not particularly limited.

The shape (shape when viewed from above), size, and the like of the first storage part 171 are not particularly limited as long as the catheter hub 313 or the catheter main body 311 can be disposed and the catheter hub 313 or the catheter main body 311 can be held. Similarly, the shape (shape when viewed from above), size, and the like of the third storage part 173 are not particularly limited as long as the dilator hub 323 or the dilator main body 321 can be disposed and the dilator hub 323 or the dilator main body 321 can be held.

As shown in FIG. 3, the first storage part 171 has a fixing part 171a for fixing the catheter member 310 in a state in which the distal end 311a of the catheter main body 311 is not in contact with the lower face part 132 (the state shown in FIG. 2).

The fixing part 171a has a plurality of slits (cuts) formed around the first storage part 171 in the support part 160. The catheter hub 313 is disposed in the first storage part 171 such that the first storage part 171 is expanded by a slit of the fixing part 171a. Therefore, the fixing part 171a prevents the catheter hub 313 from accidentally falling out of the support part 160 in a state in which the catheter hub 313 is inserted and fitted into the first storage part 171.

As shown in FIG. 3, the third storage part 173 has a function as a fixing part for fixing the dilator member 320 in a state in which the distal end 321a of the dilator main body 321 is not in contact with the lower face part 132 (the state shown in FIG. 2). The fixing of the dilator member 320 by the third storage part 173 does not firmly fix the dilator member 320, but holds the dilator member 320 in a state of being loosely fitted to the support part 160.

In a manner similar to the first storage part 171, the third storage part 173 can be configured to have a fixing part (slit or the like) for firmly fixing the dilator member 320.

As shown in FIG. 2, each side face part 121, 122, 123, and 124 is formed so that the length from the upper face part 131 to the lower face part 132 (length in the vertical direction in FIG. 2) is longer than the length from the third storage part 173 to the distal end 321a of the dilator main body 321 disposed in the third storage part 173. Therefore, the dilator member 320 is a configured or sized in a manner which can prevent the distal end 321a of the dilator main body 321 from coming into contact with the lower face part 132 in a state in which the dilator main body 321 is disposed in the third storage part 173.

As shown in FIGS. 1 and 3, the second storage part 172 is formed on the upper face part 131 side by a second hole part (second hole) that allows the second space 110B to communicate with the outside of the second space 110B. In the present embodiment, the second storage part 172 is an opening portion formed in the upper face part 131.

As shown in FIG. 1, the catheter member 310 is disposed such that the proximal portion of the catheter hub 313 and a part of the tube member 315 protrude from the upper face part (opening portion) 131 of the storage container 100 in a state in which the catheter hub 313 is disposed in the first storage part 171 and the tube member 315 is disposed in the second storage part 172. Further, the dilator member 320 is disposed such that the proximal portion of the dilator hub 323 protrudes from the upper face part (opening portion) 131 of the storage container 100 in a state in which the dilator hub 323 is disposed in the third storage part 173. As shown in FIG. 2, portions of the catheter member 310 and the dilator member 320 protruding from the upper face part 131 of the storage container 100 are covered by the cap member 140 in a state in which the cap member 140 is interlocked with the storage container 100.

The dilator member 320 disposed between the catheter main body 311 and the tubular member 315 suppresses the movement (twist) of the tubular member 315. Thereby, the dilator member 320 can prevent the tubular member 315 from being damaged by vibration during transport of the medical instrument set 10 or the like.

As shown in FIG. 2, the storage container 100 is formed such that the length of the portion of the catheter hub 313 protrudes from the upper face part 131 in a state in which the catheter hub 313 is disposed in the first storage part 171 and the length of the portion of the dilator hub 323 protrudes from the upper face part 131 in a state in which the dilator hub 323 is disposed in the third storage part 173 are substantially the same.

As shown in FIG. 3, the third storage part 173 is disposed between the first storage part 171 and the second storage part 172 when the storage container 100 is viewed from above. The center of the third storage part 173 (the center of the third hole part) is not disposed on a straight line s1 that connects the center c1 of the first storage part 171 (the center of the first hole part) and the center c2 of the second storage part 172 (the position where diagonal lines indicated by broken lines intersect with each other when viewed from above). Therefore, the storage container 100 can prevent the tube member 315 and the dilator hub 323 from interfering with each other and causing a three-dimensional obstacle in a state in which the catheter hub 313 is disposed in the first storage part 171, the tube member 315 is disposed in the second storage part 172, and the dilator hub 323 is disposed in the third storage part 173. Note that, preferably, the third storage part 173 can be configured not to be disposed on the straight line s1 that connects the center c1 of the first storage part 171 (the center of the first hole part) and the center c2 of the second storage part 172 (the position where diagonal lines indicated by broken lines intersect with each other when viewed from above).

As shown in FIG. 2, the width L2 of the second space 110B has a size such that a gap through which the accessories 330, 340, and 350 can pass is not formed between the connector unit 316 and the partition part 175 and the connector unit 316 and the inner face of the third side face part 123 in a state in which the connector unit 316 and the accessories 330, 340, and 350 are accommodated in the second space 110B. By forming the width L2 with such a size, it is possible to preferably prevent the accessories 330, 340, and 350 from moving toward the lower face part 132 beyond the connector unit 316 in a state in which the connector unit 316 and the accessories 330, 340, and 350 are accommodated in the second space 110B.

As shown in FIGS. 1 and 3, the storage container 100 has a fourth storage part 174 formed outside the first space 110A and the second space 110B. The guide wire 360 can be disposed in the fourth storage part 174.

As shown in FIG. 3, the fourth storage part 174 is formed between the second side face part 122 and a fifth side face part 125 disposed facing the second side face part 122. Similar to the first storage part 171, the fourth storage part 174 is open on the upper face part 131 side of the storage container 100 so as to face the outside of the storage container 100. Further, a third space 110C partitioned from the first space 110A and the second space 110B by the second side face part 122 is formed between the second side face part 122 and the fifth side face part 125.

As shown in FIGS. 1 and 3, the guide wire 360 can be accommodated in the third space 110C, for example, with the proximal portion side wound. Further, the distal portion of the guide wire 360 can be disposed so as to protrude from the fourth storage part 174 to the outside of the storage container 100, for example.

The inserter 180 is attached near the distal portion of the guide wire 360. The inserter 180 is made of a known material used in a procedure using the guide wire 360. The distance between the second side face part 122 and the fifth side face part 125 is smaller than the dimension of the outer shape of the inserter 180 (dimensions of the linear distance such as vertical and horizontal directions in the top view shown in FIG. 3). Therefore, the inserter 180 is interposed between the second side face part 122 and the fifth side face part 125 in a state in which the distal portion of the guide wire 360 is disposed in the fourth storage part 174. The guide wire 360 is fixed to each of the side face parts 122 and 125 by the inserter 180 being interposed between the second side face part 122 and the fifth side face part 125. As described above, the inserter 180 can be used as a fixing member for fixing the guide wire 360 to the side face parts 122 and 125 or fixing the position of the guide wire 360 relative to the side face parts 122 and 125.

The fixing member may be configured by, for example, a clip that can fix the guide wire 360 to the second side face part 122, the fifth side face part 125, or the like, a fixing mechanism (a mechanism that can fix the guide wire 360 with a groove or gripping mechanism) formed in the storage container 100, or the like.

Each part (each side face part 121 to 125, lower face part 132, partition part 175, support part 160, and the like) of the storage container 100 may be integrally formed by, for example, molding or the like, may be formed by joining parts formed of different members by a method such as adhesion or welding, or may be one obtained by mechanically interlocking components formed of different members. Further, the material constituting each part of the storage container 100 is not particularly limited. Examples thereof include polymer materials such as nylon, polyacrylamide, polycarbonate, polyethylene, polyformaldehyde, polymethyl methacrylate, polypropylene, polystyrene, polytetrafluoroethylene, polytrifluorochloroethylene, polyvinyl chloride, polyurethane, polyether block amide, and elastomer organic silicon polymers, or other resin materials, metal materials (such as stainless steel and Nitinol), and paper materials. It is preferable that the second side face part 122 and the fifth side face part 125 are made of a material having a hardness low enough to be deformed when the inserter 180 is pressed against. Examples of such a material include polyethylene, polypropylene, and polystyrene.

The storage container 100 may be configured so that the support part 160 is detachable from the first space 110A of the storage container 100, for example, when the support part 160 includes a member different from other parts (side face parts 121 to 125, lower face part 132, partition part 175, and the like) of the storage container 100. When the support part 160 is configured to be detachable from the first space 110A of the storage container 100, the catheter member 310 can be removed from the storage container 100 together with the support part 160 in a state in which the catheter member 310 is fixed to the support part 160 via the fixing part 171a. Therefore, because the catheter member 310 can be removed from the support part 160 in a state in which the support part 160 is removed from the storage container 100, the catheter member 310 can be more easily removed while preventing it from interfering with other members in the packaging member 200.

Next, the cap member 140 will be described.

As shown in FIGS. 1 and 2, the cap member 140 can be interlocked with the storage container 100 from the upper face part 131 of the storage container 100. The cap member 140 protects the catheter member 310, the dilator member 320, and the guide wire 360 exposed from the upper face part 131 of the storage container 100. Inside the cap member 140, a space is formed to cover one end (upper end) of each of the side face parts 121, 122, 123, and 125 of the storage container 100.

As shown in FIG. 2, in a state in which the cap member 140 is interlocked with the storage container 100, an inner face 141 on the upper end side of the cap member 140 comes into contact with the proximal end of the catheter hub 313 and the proximal end of the dilator hub 323.

The cap member 140 can also be configured to come into contact with only one of the proximal end of the catheter hub 313 and the proximal end of the dilator hub 323. When the cap member 140 is configured to come into contact with only one of the proximal end of the catheter hub 313 and the proximal end of the dilator hub 323, the packaging member 200 is configured to fix the catheter hub 313 or the dilator hub 323 by the cap member 140. Thereby, the packaging member 200 can prevent the catheter member 310 or the dilator member 320 from being accidentally moved due to vibration during transport or the like.

By way of example, the cap member 140 may be configured so as not to be in contact with both the proximal end of the catheter hub 313 and the proximal end of the dilator hub 323 in a state of being interlocked with the storage container 100.

The material constituting the cap member 140 is not particularly limited. Examples thereof include the same material as the material constituting the aforementioned storage container 100.

The storage container 100 and the cap member 140 are preferably formed to be transparent or translucent as the catheter member 310, the dilator member 320, the accessories 330, 340, 350, and the guide wire 360 accommodated inside the storage container 100 and the cap member 140 can be visually recognized from the outside, for example, in a state in which the medical instrument set 10 is configured.

Next, the seal member 150 will be described.

Figure 4:
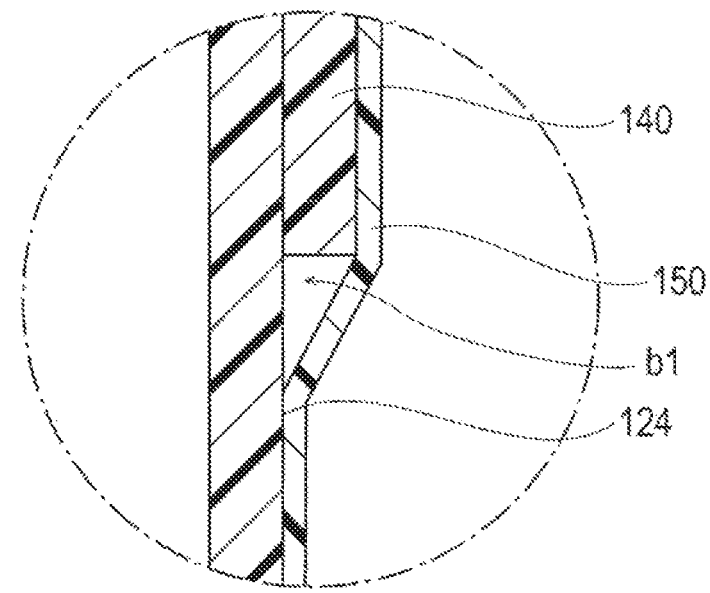
FIG. 4 is an enlarged cross-sectional view of a portion indicated by a one-dot chain line 4A in FIG. 2.

In the present embodiment, the seal member 150 is formed of an elongated tape having an adhesive layer having adhesiveness formed on the inner face side. As shown in FIG. 4, the seal member 150 is disposed such that the inner face having adhesiveness is attached to the storage container 100 and the cap member 140. The seal member 150 covers a boundary part b1 between the storage container 100 and the cap member 140 while interlocking the storage container 100 with the cap member 140.

The seal member 150 is made of a material having a sterilized gas permeability that allows a sterilizing gas such as ethylene oxide gas (EOG) to pass therethrough. The material of the seal member 150 is not particularly limited, and examples thereof include a paper material and a polyolefin-based nonwoven fabric. By configuring the seal member 150 with such a material, the sterilizing gas passes through the seal member 150, enters between the cap member 140 and the storage container 100, and so the introducer 300, the accessories 330, 340, 350, the guide wire 360, the inner face of the storage container 100, and the inner face of the cap member 140 can be (are) sterilized.

For example, when using the introducer 300, the accessories 330, 340, 350, and the guide wire 360 accommodated in the packaging member 200, the operator performs the following operation.

First, the operator removes the seal member 150. Next, the operator removes the cap member 140 from the storage container 100. Next, the operator tilts the upper face part 131 of the storage container 100 downward (downward in the direction of gravity). Since the dilator hub 323 is loosely fitted in the third storage part 173, the dilator member 320 can be easily removed by tilting the storage container 100. Further, at this time, the accessories 330, 340, and 350 disposed in the second space 110B are easily taken out of the storage container 100 via the second storage part 172. Next, the operator can remove the catheter member 310 from the storage container 100 by lifting the catheter hub 313 of the catheter member 310 with fingers or the like. Further, the operator can easily remove the guide wire 360 from the storage container 100 by releasing the fixation of the guide wire 360 by the inserter 180.

As described above, the storage container 100 according to the present embodiment is a storage container for accommodating the introducer 300 including the catheter member 310 having the catheter main body 311, the catheter hub 313 disposed at a proximal portion of the catheter main body 311, the tubular member 315 disposed on the side face side of the catheter hub 313 and communicating with the lumen of the catheter hub 313, and the connector unit 316 disposed at the end portion of the tube member 315 opposite to the catheter hub 313 and the dilator member 320 having the dilator main body 321 that can be inserted into the lumen of the catheter main body 311 and the dilator hub 323 disposed at the proximal portion of the dilator main body 321. The storage container 100 includes each side face parts 121, 122, 123, and 124 surrounding the first space 110A and the second space 110B for accommodating the introducer 300, the first storage part 171 in which the catheter hub 313 is disposed, the second storage part 172 in which the tube member 315 is disposed in a state in which the connector unit 316 is disposed in the second space 110B, and the third storage part 173 in which the dilator hub 323 is disposed. The third storage part 173 is disposed between the first storage part 171 and the second storage part 172.

In the above-described storage container 100, the catheter main body 311 or the catheter hub 313 is disposed in the first storage part 171, the tubular member 315 is disposed in the second storage part 172 and the dilator main body 321 or the dilator hub 323 is disposed in the third storage part 173. Further, the third storage part 173 is located between the first storage part 171 and the second storage part 172. Therefore, the above-described storage container 100 can three-dimensionally accommodate the catheter member 310 and the dilator member 320, and can reduce the volume (size) of the storage container 100. Further, because the catheter main body 311 or the catheter hub 313 is disposed in the first storage part 171 and the tubular member 315 is disposed in the second storage part 172, the distance between the catheter main body 311/catheter hub 313 positioned in the first storage part 171 and the tubular member 315 positioned in the second storage part 172 is increased compared to a situation in which the second storage part 172 is between the first and third storage parts 171, 173. Kinking of the tubular member 315 due to a relatively short distance between the catheter main body 311/catheter hub 313 and the tubular member 315 can be prevented. Furthermore, in the above-described storage container 100, the catheter member 310 and the dilator member 320 can be disposed close to each other in a state in which the orientation of the catheter member 310 and the orientation of the dilator member 320 forming the introducer 300 (assembly) with the catheter member 310 are in the same direction, so that the operator can easily assemble the catheter member 310 and the dilator member 320.

Further, the third storage part 173 is not disposed on the straight line s1 that connects the center c1 of the first storage part 171 and the center c2 of the second storage part 172. Therefore, it is possible to prevent the tubular member 315 extending from the catheter hub 313 disposed in the first storage part 171 toward the second storage part 172 from interfering with the dilator hub 323 disposed in the third storage part 173 and causing a three-dimensional obstacle.

Further, the storage container 100 has the fourth storage part 174 formed outside the first space 110A and the second space 110B and in which the guide wire 360 is disposed and the inserter (fixing member) 180 for fixing the guide wire 360 to the second side face part 122 and the fourth side face part 124. Therefore, the storage container 100 can accommodate the guide wire 360 together with the introducer 300 without causing the guide wire 360 to interfere with the introducer 300.

Further, the storage container 100 has the upper face part 131 formed inside each of the side face parts 121, 122, 123, and 124 and on one end side of each of the side face parts 121, 122, 123, and 124, and the lower face part 132 opposed to the upper face part 131 with the side face parts 121, 122, 123, and 124 interposed therebetween. The first storage part 171 is a first hole part that allows the first space 110A to communicate with the outside of the first space 110A on the upper face part 131 side, the second storage part 172 is a second hole part that allows the first space 110A to communicate with the outside of the first space 110A on the upper face part 131 side, and the third storage part 173 is a third hole part on the upper face part 131 side, that allows the second space 110B to communicate with the outside of the second space 110B. The first storage part (first hole part) 171 has the fixing part 171a for fixing the catheter member 310 in a state in which the distal end 311a of the catheter main body 311 is not in contact with the lower face part 132. The third storage part (third hole part) 173 functions as a fixing part for fixing the dilator member 320 in a state in which the distal end 321a of the dilator main body 321 does not come into contact with the lower face part 132. Therefore, when transported in a state in which the catheter member 310 and the dilator member 320 are accommodated in the storage container 100, the storage container 100 can prevent the distal end 311a of the catheter main body 311 from being damaged by coming into contact with the lower face part 132, and can prevent the distal end 321a of the dilator main body 321 from being damaged by coming into contact with the lower face part 132.

Further, the packaging member 200 includes the storage container 100, the cap member 140 that protects the catheter member 310 and the dilator member 320 exposed from the upper face part 131 of the storage container 100, and the seal member 150 that covers the boundary part b1 between the storage container 100 and the cap member 140 while interlocking the storage container 100 with the cap member 140. The seal member 150 has sterilizing gas permeability. Therefore, the packaging member 200 allows the catheter member 310 and the dilator member 320 to be sterilized without covering the storage container 100 with a bag or bag member (peel bag or the like). Thereby, the packaging member 200 can reduce the size of the packaging member 200. Further, after sterilizing the catheter member 310 and the dilator member 320, the packaging member 200 can prevent the inside of the storage container 100 and the cap member 140 from being contaminated by the seal member 150.

Further, in the packaging member 200, the cap member 140 comes into contact with the catheter hub 313 and the dilator hub 323 in a state in which the storage container 100 and the cap member 140 are interlocked. Therefore, the packaging member 200 can fix the catheter hub 313 and the dilator hub 323 by the cap member 140. Thereby, the packaging member 200 can prevent the catheter member 310 and the dilator member 320 from being accidentally moved due to vibration during transport or the like.

Further, the medical instrument set 10 includes the packaging member 200, the introducer 300, and the accessories 330, 340, and 350 accommodated in the second space 110B and having a width smaller than the maximum width L1 of the connector unit 316 in a direction intersecting the axial direction of the tubular member 315. Since the medical instrument set 10 has the packaging member 200 in which the accessories 330, 340, and 350 are accommodated together with the introducer 300, preparation of a procedure using the introducer 300 can be smoothly performed. Further, in the state in which the accessories 330, 340, and 350 are accommodated in the second space 110B, the position in the second space 110B is held by the connector unit 316 of the catheter member 310. Since the accessories 330, 340, and 350 are not firmly fixed to the packaging member 200, the operator can easily remove the accessories 330, 340, and 350 from the packaging member 200.

Modification Example

Next, a modification example of the aforementioned embodiment will be described. Features in this modification example that are the same as features described above are identified by common reference numeral and a detailed description of such features is not repeated.

Figure 5:
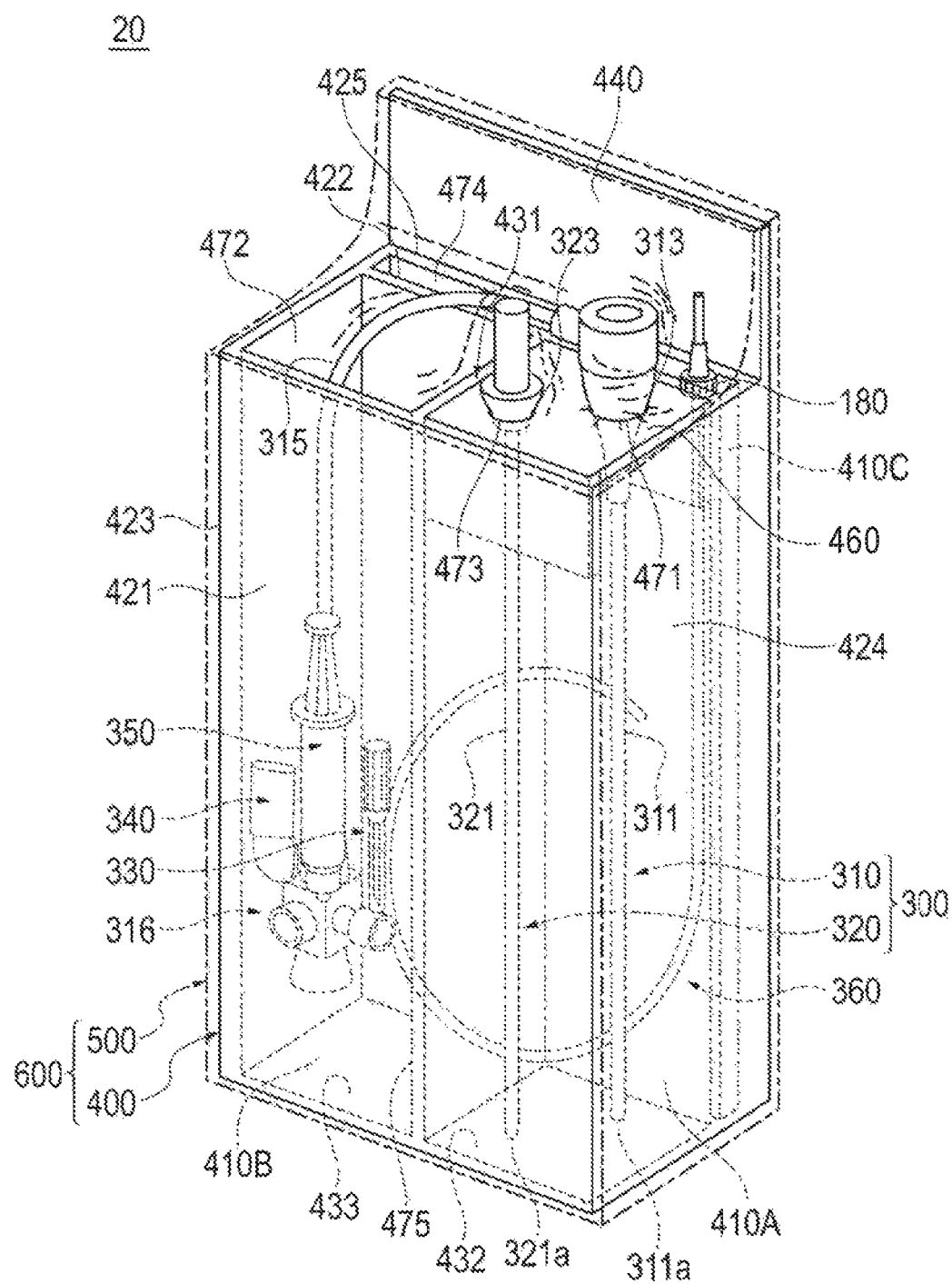
FIG. 5 is a schematic perspective view showing a medical instrument set according to a modification example.
Figure 6:
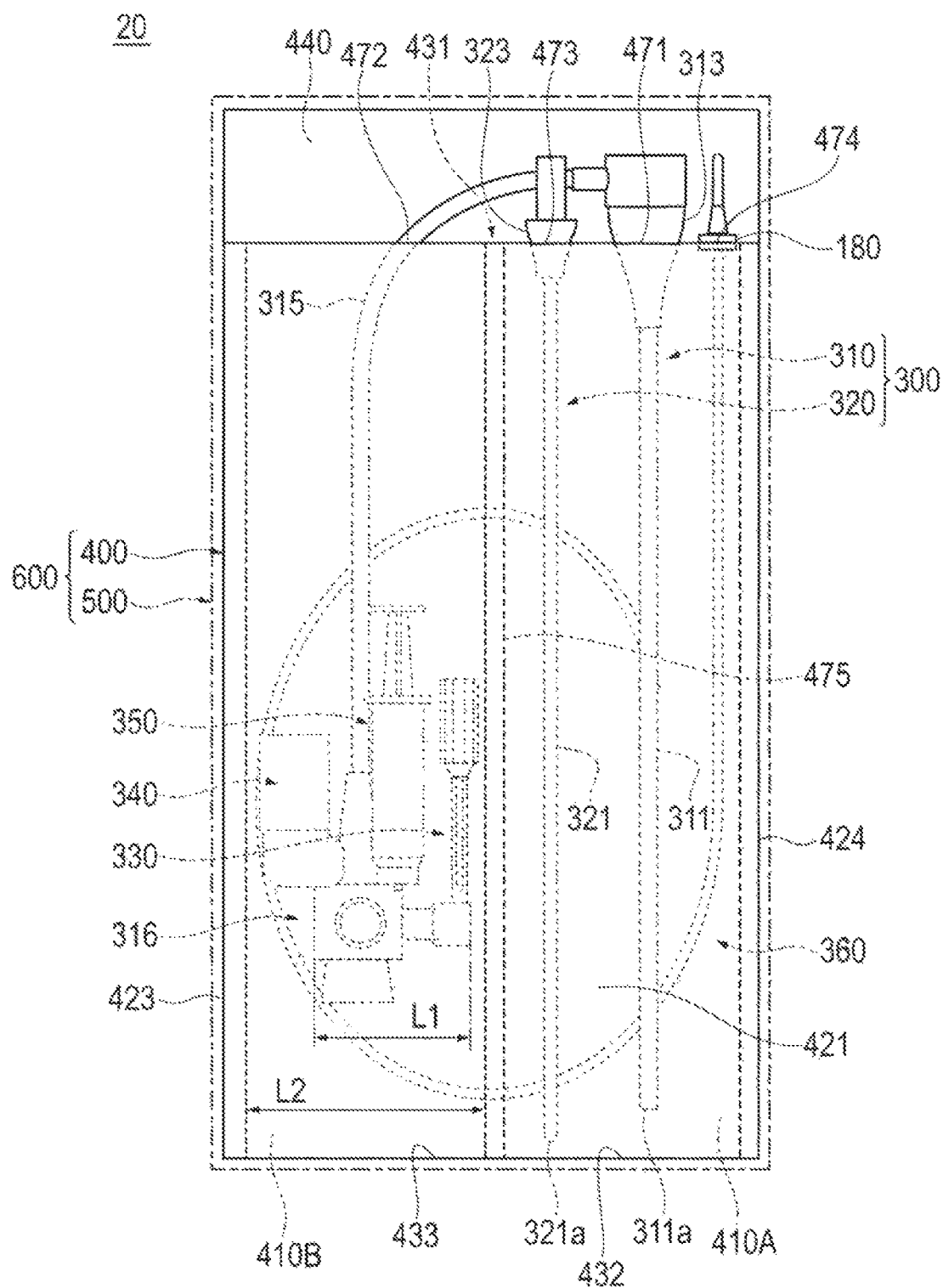
FIG. 6 is a front view of a medical instrument set according to the modification example.
Figure 7:
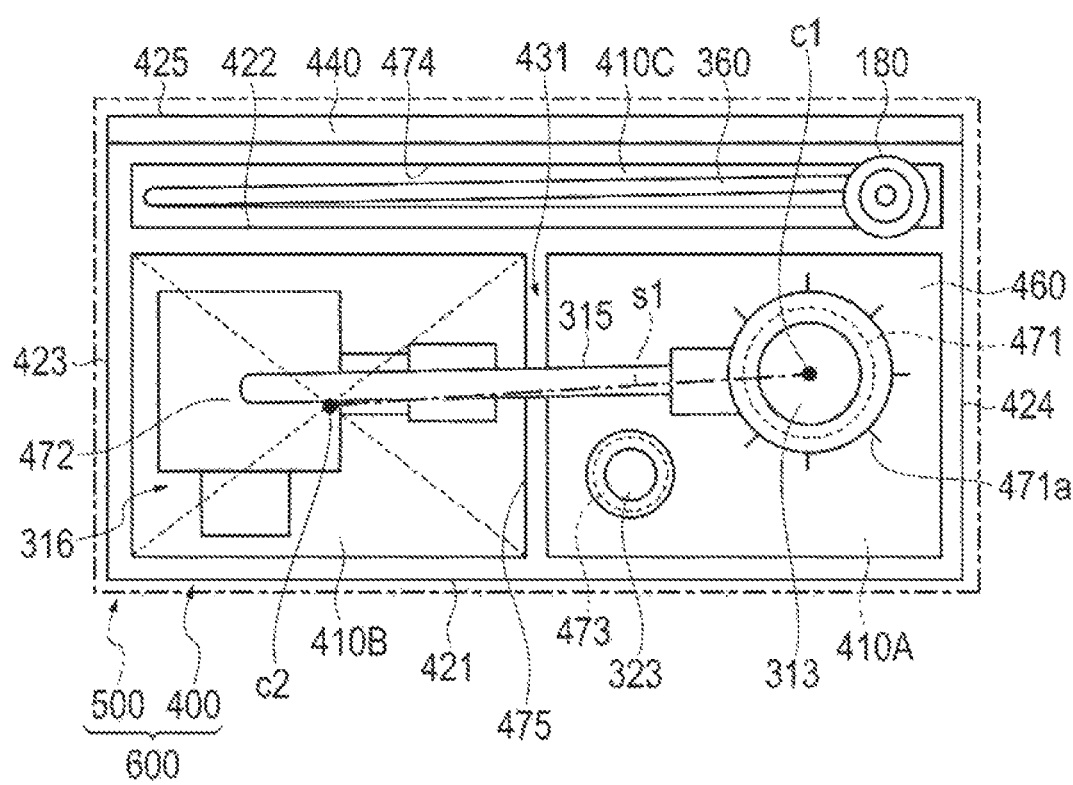
FIG. 7 is a top view of a medical instrument set according to the modification example.

FIGS. 5 to 7 show a medical instrument set 20 according to a modification example. FIG. 5 is a schematic perspective view of the medical instrument set 20, FIG. 6 is a front view of the medical instrument set 20, and FIG. 7 is a top view of the medical instrument set 20. In each drawing, a bag or bag member 500 is indicated by a one-dot chain line in order to clarify the positional relationship between the members. Further, illustration of the accessories 330, 340, and 350 is omitted in FIG. 7.

As shown in FIGS. 5 and 6, a packaging member 600 included in the medical instrument set 20 according to the modification example includes a storage container 400 and the bag member 500. The packaging member 600 does not include the cap member 140 and the seal member 150 (see FIG. 2) included in the packaging member 200 according to the above-described embodiment.

Further, as shown in FIG. 6, the storage container 400 according to the modification example has lower face opening portions 432 and 433. That is, the storage container 400 does not have a bottom portion.

As shown in FIGS. 5 to 7, the storage container 400 includes a first space 410A that accommodates the catheter main body 311 and the dilator main body 321, a second space 410B that accommodates the tubular member 315 and the accessories 330, 340, and 350, and a first side face part 421, a second side face part 422, a third side face part 423, and a fourth side face part 424 surrounding the first space 410A and the second space 410B.

As shown in FIG. 5, the storage container 400 includes an upper face part 431 formed inside each of the side face parts 421, 422, 423, and 424 (on the first space 410A and the second space 410B side), and one end (upper end side) of each of the side face parts 421, 422, 423, and 424, and the lower face opening portions 432 and 433 facing the upper face part 431 with the side face parts 421, 422, 423, and 424 interposed therebetween.

As shown in FIG. 6, the first space 410A and the second space 410B are partitioned by a partition part 475. The partition part 475 is disposed substantially parallel to the side face parts 423 and 424. The lower face opening portion 432 allows the first space 410A to communicate with the outside of the storage container 400. Further, the lower face opening portion 433 allows the second space 410B to communicate with the outside of the storage container 400.

As shown in FIGS. 5 and 7, the storage container 400 has a fourth storage part 474 formed outside the first space 410A and the second space 410B. The guide wire 360 can be disposed in the fourth storage part 474. A third space 410C partitioned from the first space 410A and the second space 410B by the second side face part 422 is formed between the second side face part 422 and a fifth side face part 425.

A first storage part 471 is a first hole part on the upper face part 431 side that allows the first space 410A to communicate with the outside of the first space 410A. The first storage part 471 is formed in a support part 460. The first storage part 471 has a fixing part 471a as shown in FIG. 7. The fixing part 471a fixes the catheter member 310 in a state in which the distal end 311a of the catheter main body 311 does not protrude from (beyond) the lower face opening portion 432 (the state shown in FIG. 6).

A third storage part 473 is a third hole part on the upper face part 431 side that allows the first space 410A to communicate with the outside of the first space 410A. The third storage part 473 is formed in the support part 460. The third storage part 473 functions as a fixing part for fixing the dilator member 320 in a state in which the distal end 321a of the dilator main body 321 does not protrude from (beyond) the lower face opening portion 432 (the state shown in FIG. 6).

A second storage part 472 is a second hole part communicating the upper face part 431 and the second space 410b.

A backrest part 440 extending in the height (vertical) direction (upward in FIG. 6) is formed on the back of the storage container 400 (the back of the fifth side face part 425). When the medical instrument set 20 is transported or the like, the backrest part 440 prevents the article from colliding with the catheter member 310 or the dilator member 320, or preventing the catheter member 310 or the dilator member 320 from being damaged due to vibration during transport or the like.

The packaging member 600 has the bag member 500 that covers the storage container 400 in a state in which the storage container 400 accommodates the catheter member 310, the dilator member 320, the accessories 330, 340, 350, and the guide wire 360.

The bag member 500 is a bag capable of maintaining a sterilized state with the storage container 400 and the like accommodated inside the bag member 500. The bag member 500 can be composed of a bag having a sterilizing gas permeability that allows a sterilizing gas such as ethylene oxide gas (EOG) to pass therethrough. As the bag member 500 having such performance, for example, a known peel bag can be used.

In the medical instrument set 20 according to the present modification example, when sterilizing the medical instrument set 20, gas for sterilization permeates the bag member 500 and flows into each of the spaces 410A, 410b, 410C of the storage container 400 via the lower face opening portions 432 and 433 of the storage container 400. Therefore, the medical instrument set 20 can efficiently perform gas sterilization of the catheter member 310, the dilator member 320, the accessories 330, 340, 350, and the guide wire 360.

Further, as shown in FIG. 6, in the medical instrument set 20, the distal end 311a of the catheter main body 311 and the top of the distal end 321a of the dilator main body 321 do not protrude from the lower face opening portion 432. Therefore, the medical instrument set 20 can prevent the distal end 311a of the catheter main body 311 and the distal end 321a of the dilator main body 321 from damaging the bag member 500 due to vibration during transport or the like.

The storage container, packaging member, and medical instrument have been described through the embodiment and the modification example representing examples of the inventive storage container, packaging member, and medical instrument disclosed here. However, the present invention is not limited to only the configurations described in the embodiment and the modification example, and can be appropriately modified.

For example, the size, external shape, and the like of the storage container can be appropriately changed according to the type of medical instrument to be accommodated. For example, the outer shape of the storage container is not limited to a cube, and may be a column or the like.

Further, for example, in the storage container, it is possible to omit the formation of the fourth storage part and the third space for disposing and accommodating the guide wire.

Further, for example, the space for accommodating medical instruments and accessories does not have to be a plurality of spaces partitioned by the partition part like the first space and the second space, and may be formed by, for example, one space. Similarly, when the storage container is configured to be capable of accommodating a guide wire, the first space, the second space, and the third space may be formed as one space without partitions. Further, each storage part is not limited to the shape described in the drawings (the shape in plan view). For example, the second storage part may be configured by a circular, elliptical, rectangular, or other hole formed in a part of the upper face part of the storage container.

Further, for example, the medical instrument is not limited to the introducer, and the catheter member may be a catheter device having a function as a guiding catheter, a guiding sheath, or the like.

The detailed description above describes embodiments of a storage container, packaging member, and medical instrument representing examples of the inventive storage container, packaging member, and medical instrument disclosed here. The invention is not limited, however, to the precise embodiment, modification and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

REFERENCE SIGNS LIST 10, 20 medical instrument set
100 storage container
110A first space (space)
110B second space (space)
110C third space
121 first side face part (side face part)
122 second side face part (side face part)
123 third side face part (side face part)
124 fourth side face part (side face part)
125 fifth side face part
131 upper face part
132 lower face part
140 cap member
141 inner face of cap member
150 seal member
160 support part
171 first storage part (first hole part)
171a fixing part
172 second storage part (second hole part)
173 third storage part (third hole part)
174 fourth storage part
175 partition part
180 inserter (fixing member)
200 packaging member
300 introducer (medical instrument)
310 catheter member
311 catheter main body
311a distal end of catheter main body
313 catheter hub
315 tubular member
316 connector unit 320 dilator member
321 dilator main body
321a distal end of dilator main body
323 dilator hub
330, 340, 350 accessory
360 guide wire
400 storage container
410A first space (space)
410B second space (space)
410C third space
421 first side face part (side face part)
422 second side face part (side face part)
423 third side face part (side face part)
424 fourth side face part (side face part)
425 fifth side face part
431 upper face part
432, 433 lower face opening portion
440 backrest part
460 support part
471 first storage part (first hole part)
471a fixing part
472 second storage part (second hole part)
473 third storage part (third hole part)
474 fourth storage part
475 partition part
500 bag member
600 packaging member
L1 maximum width of connector unit
L2 width of second space
b1 boundary part between storage container and cap member
c1 center of first storage part
c2 center of second storage part

What is claimed is:

1. A storage container configured to accommodate a medical instrument that comprises: a catheter member and a dilator member, the catheter member including a catheter main body, a catheter hub disposed at a proximal portion of the catheter main body, a tubular member disposed on a side face of the catheter hub and communicating with a lumen of the catheter hub and a connector unit disposed at an end portion of the tubular member opposite to the catheter hub, the dilator member including a dilator main body insertable into a lumen of the catheter main body and a dilator hub disposed at a proximal portion of the dilator main body, the storage container comprising:
    a side face part surrounding an internal space that is configured to accommodate the medical instrument, the internal space extending in an axial direction of the storage container from a first end of the storage container to an open second end of the storage container, the internal space being comprised of a first internal space and a second internal space that are separated from each other by a partition that extends in the axial direction of the storage container so that the first internal space is located on a first side of the partition and the second internal space is located on a second side of the partition;
    a support part positioned on the first side of the partition and extending across the first internal space so that the support part overlies at least a part of the internal space and the at least a part of the internal space is located between the first end of the storage container and the support part;
    a catheter hole passing through the support part and forming a first storage part configured to receive the catheter main body or the catheter hub;
    a second storage part located on the second side of the partition and configured to receive the tubular member while the connector unit is disposed in the internal space;
    a dilator hole passing through the support part and forming a third storage part configured to receive the dilator main body or the dilator hub; and
    the third storage part is disposed between the first storage part and the second storage part.

2. The storage container according to claim 1, wherein the is positioned so that a straight line connecting a center of the first storage part and a center of the second storage part does not pass through the third storage part as viewed from the open second end of the storage container.

3. The storage container according to claim 1, wherein the side face part includes a plurality of walls extending in the axial direction of the storage container from the first end of the storage container to the open second end of the storage container, further comprising:
    a fourth storage part separated from the internal space by one of the walls and configured to receive a guide wire; and
    a fixing member configured to fix the guide wire to the side face part.

4. The storage container according to claim 1, wherein the side face part includes
    a lower face part that is the first end of the storage container defining a closed end and that faces towards the first internal space
    the support part being positioned at the open second end of the storage container so that when the dilator main body is positioned in the dilator hole a distal end of the dilator main body is not in contact with the lower face part and so that when the catheter main body is positioned in the catheter hole a distal end of the catheter main body is not in contact with the lower face part.

5. The storage container according to claim 1, wherein the side face part includes a first wall, a second wall, a third wall and a fourth wall that each extend in the axial direction of the storage container, the first and second walls being positioned parallel to and opposite one another, the third and fourth walls being positioned parallel to and opposite one another, the first and second walls being positioned parallel to the partition.

6. The storage container according to claim 5, wherein the catheter hole possesses a center and the dilator hole possesses a center, and a straight line connecting the center of the catheter hole and a center of the second internal space as seen from the open second end of the storage container does not pass through the center of the dilator hole.

7. The storage container according to claim 5, wherein the storage container is a parallelepiped possessing a largest dimension in a direction parallel to the first, second, third and fourth walls.

8. The storage container according to claim 5, further comprising:
    a third space separated from both the first internal space and the second internal space by the second wall;
    the third space being at least partially enclosed by the second wall and a fifth wall parallel to the second wall, the third space being configured to receive a guide wire.

9. The storage container according to claim 1, wherein the first end of the storage container is an open first end of the storage container, the second internal space having opposite ends that are open.

10. A packaging member packaging a medical instrument that comprises a catheter member and a dilator member, the catheter member including a catheter main body, a catheter hub disposed at a proximal portion of the catheter main body, a tubular member disposed on a side face of the catheter hub and communicating with a lumen of the catheter hub and a connector unit disposed at an end portion of the tubular member opposite to the catheter hub, the dilator member including a dilator main body insertable into a lumen of the catheter main body and a dilator hub disposed at a proximal portion of the dilator main body, the packaging member comprising:
- a storage container comprising:
  - a side face part surrounding an internal a space in which is disposed the connector unit, the internal space extending in an axial direction of the storage container from a first end of the storage container to an open second end of the storage container, the internal space being comprised of a first internal space and a second internal space that are positioned on opposite sides of a plane that extends in the axial direction of the storage container so that the first internal space is located on a first side of the plane and the second internal space is located on a second side of the plane;
  - a first storage part located on the first side of the plane, the catheter main body or the catheter hub being held by the first storage part so that the catheter main body and the catheter hub are located on the first side of the plane and so that a distal portion of the catheter main body that projects away from the catheter hub extends towards the first end of the storage container;
  - a second storage part that communicates with the second internal space, at least a part of the tubular member being positioned in the second internal space, the plane intersecting the tubular member;
  - a third storage part located on the first side of the plane, the dilator main body or the dilator hub being held by the third storage part so that the dilator main body and the dilator hub are located on the first side of the plane and so that a distal portion of the dilator main body that projects away from the dilator hub extends towards the first end of the storage container;
  - the third storage part being disposed between the first storage part and the second storage part; and
  - the internal space and the medical instrument being enclosed and being prevented from communicating with an outside space that is outside the packaging member so that the internal space and the medical instrument remain in a sterilized state when sterilized.

11. The packaging member according to claim 10, wherein the internal space, the catheter member and the dilator member are sterilized.

12. The packaging member according to claim 10, further comprising:
- a cap member removably mounted on the storage container to cover the open second end and protect the medical instrument, the cap member being mounted on the storage container so that a boundary exists between the storage container and the cap member;
- a seal member covering the boundary between the storage container and the cap member, the seal member fixing the cap member on the storage container; and
- the seal member being permeable to sterilizing gas.

13. The packaging member according to claim 12, wherein the cap member possesses an inner surface facing toward the first and second internal spaces, the inner surface of the cap member being in contact with at least one of the catheter hub and the dilator hub.

14. The packaging member according to claim 10, wherein the side face part includes a first wall, a second wall, a third wall and a fourth wall, the first and second walls being positioned parallel to and opposite one another, the third and fourth walls being positioned parallel to and opposite one another, the first internal space and the second internal space being separated from one another by a partition wall that lies in the plane and that is positioned between the first and second internal spaces, the connector unit being positioned in the second internal space.

15. The packaging member according to claim 10, further comprising a support part overlying at least a part of the first internal space, the first storage part being a first hole passing through the support part, the first hole possessing a center, the third storage part being an other hole passing through the support part, the other hole possessing a center, and a straight line connecting the center of the first hole and a center of the second internal space as seen from the one end does not pass through the center of the other hole.

16. The packaging member according to claim 10, wherein the side face part includes a first wall, a second wall, a third wall and a fourth wall, the first and second walls being positioned parallel to and opposite one another, the third and fourth walls being positioned parallel to and opposite one another, the storage container being a parallelepiped possessing a largest dimension in the axial direction that is parallel to the first, second, third and fourth walls.

17. The packaging member according to claim 10, wherein the side face part includes a first wall, a second wall, a third wall and a fourth wall, the first and second walls being positioned parallel to and opposite one another, the third and fourth walls being positioned parallel to and opposite one another, the first internal space and the second internal space being separated from one another by a partition wall that lies in the plane and that is positioned between the first and second spaces, and further comprising a third space separated from both the first internal space and the second internal space by the second wall, the third space being at least partially enclosed by the second wall and a fifth wall parallel to the second wall, and a guide wire positioned in the third space.

18. The packaging member according to claim 10, wherein the first storage part is a first hole that communicates the first internal space with an outside space that is outside the first internal space, the second storage part being a second hole that communicates the second internal space with the outside space, the third storage part being a third hole that communicates the second internal space with the outside, the first hole and the third hole each passing through a support part that is removably positioned in the first internal space; and
- a bag member enclosing the storage container and the medical instrument which is sterilized, the bag member maintaining the medical instrument in a sterilized state while the medical instrument is enclosed in the bag member, and the bag member being permeable to sterilizing gas.

19. A medical instrument set comprising:
- a medical instrument comprised of a catheter member and a dilator member, the catheter member including a catheter main body, a catheter hub disposed at a proximal portion of the catheter main body, a tubular member disposed on a side face of the catheter hub and communicating with a lumen of the catheter hub and a connector unit disposed at an end portion of the tubular member opposite to the catheter hub, the dilator member including a dilator main body insertable into a lumen of the catheter main body and a dilator hub disposed at a proximal portion of the dilator main body, a storage container comprising:
a side face part surrounding an internal a space, the internal space extending in an axial direction of the storage container from a first end of the storage container to an open second end of the storage container, the internal space being comprised of a first internal space and a second internal space that are positioned on opposite sides of a plane extending in the axial direction of the storage container so that the first internal space is located on a first side of the partition and the second internal space is located on a second side of the partition;
a support part positioned on the first side of the plane in overlying relation to at least a part of the first internal space, the support part including a catheter hole passing through the support part and a dilator hole passing through the support part, the catheter hole and the dilator hole being spaced apart from one another;
the catheter main body or the catheter hub being held in the catheter hole in the support part while at least a part of the catheter main body is positioned in the first internal space and extends towards the first end of the storage container;
the dilator main body or the dilator hub being held in the dilator hole in the support part while at least a part of the dilator main body is positioned in the first internal space and extends towards the first end of the storage container;
the tubular member passing through an open end of the second internal space in the storage container and being positioned in the second internal space, the connector unit being positioned in the second internal space;
the dilator hole being disposed between the catheter hole and the open end of the second internal space in the storage container;
an accessory accommodated in the second internal space in the storage container and having a width smaller than a maximum width of the connector unit in a direction intersecting an axial direction of the tube member.

20. The medical instrument set according to claim 19, wherein the internal space, the catheter member, the dilator member and the accessory are sterilized, the internal space, the catheter member, the dilator member and the accessory being enclosed and being prevented from communicating with an outside space that is outside the packaging member so that the internal space and the medical instrument remain in a sterilized state when sterilized.

21. The medical instrument set according to claim 19, wherein the first internal space and the second internal space that are separated from one another by a partition wall positioned between the first and second internal spaces and extending from the first end of the storage container, which is a closed end of the storage container, to the open second end of the storage container, a tubular part of the catheter main body that projects away from the catheter hub being positioned in the first internal space and extending into the second internal space, the storage container possessing a largest dimension in a direction parallel to the partition wall, the partition wall lying in the plane, and the plane intersecting the tubular part of the catheter main body.

* * * * *